United States Patent
Luzina et al.

(10) Patent No.: US 10,399,965 B2
(45) Date of Patent: Sep. 3, 2019

(54) 2-ACETYL-6-(2-(2-(4-BROMOBENZYLIDENE)HYDRAZINYL)THIAZOLE-4-YL)-3,7,9-TRIHYDROXY-8,9B-DIMETHYL-DIBENZO[,B,D]FURAN-1(9BH)-ONE EXHIBITING AN INHIBITORY EFFECT ON HUMAN TYROSYL-DNA-PHOSPHODIESTERASE 1 ENZYME

(71) Applicant: INNOVATIVE PHARMACOLOGY RESEARCH OOO (IPHAR), Tomsk (RU)

(72) Inventors: Olga Anatolyevna Luzina, Novosibirsk (RU); Alexandra Leonidovna Zakharenko, Novosibirsk (RU); Dmitry Nikolaevich Sokolov, Novosibirskaya oblast, r.p.Koltsovo (RU); Nariman Faridovich Salakhutdinov, Novosibirsk (RU); Olga Ivanovna Lavrik, Novosibirsk (RU); Veniamin Abramovich Khazanov, Tomsk (RU)

(73) Assignee: INNOVATIVE PHARMACOLOGY RESEARCH OOO (IPHAR), Tomsk (RU)

( * ) Notice: Subject to any disclaimer, the term of this patent is extended or adjusted under 35 U.S.C. 154(b) by 0 days.

(21) Appl. No.: 16/324,388

(22) PCT Filed: Jul. 24, 2017

(86) PCT No.: PCT/RU2017/000543
§ 371 (c)(1),
(2) Date: Feb. 8, 2019

(87) PCT Pub. No.: WO2018/030916
PCT Pub. Date: Feb. 15, 2018

(65) Prior Publication Data
US 2019/0177315 A1    Jun. 13, 2019

(30) Foreign Application Priority Data
Aug. 8, 2016 (RU) .................. 2016132716

(51) Int. Cl.
*C07D 417/04* (2006.01)
(52) U.S. Cl.
CPC ................... *C07D 417/04* (2013.01)
(58) Field of Classification Search
None
See application file for complete search history.

(56) References Cited

FOREIGN PATENT DOCUMENTS

RU         2612256   * 11/2017  .......... C07D 417/04

* cited by examiner

Primary Examiner — Alicia L Otton
(74) Attorney, Agent, or Firm — Dergosits & Noah LLP

(57) ABSTRACT

The present invention relates to the field of molecular biology, biochemistry and biotechnology, namely, to compound 2-acetyl-6-(2-(2-(4-bromobenzylidene)hydrazinyl)thiazole-4-yl)-3,7,9-trihydroxy-8,9b-dimethyldibenzo[b,d]furan-1(9bh)-one, which is a hydrazine-thiazole derivative of usnic acid of formula I and which is able to inhibit the action of human tyrosyl-DNA-phosphodiesterase 1 enzyme. Technical result: increase in inhibitory action towards human tyrosyl-DNA-phosphodiesterase 1 enzyme (Tdp1) and increase in the number of inhibitors of this enzyme. 1 independent claim, 2 figures, 3 examples.

1 Claim, 2 Drawing Sheets

2-ACETYL-6-(2-(2-(4-BROMOBENZYLI-DENE)HYDRAZINYL)THIAZOLE-4-YL)-3,7,9-TRIHYDROXY-8,9B-DIMETHYL-DIBENZO[,B,D]FURAN-1(9BH)-ONE EXHIBITING AN INHIBITORY EFFECT ON HUMAN TYROSYL-DNA-PHOSPHODIESTERASE 1 ENZYME

CROSS REFERENCE TO RELATED APPLICATION

This application is a U.S. National Phase of International Application No. PCT/RU2017/000543, filed on Jul. 24, 2017, which claims priority to and the benefit of Russian Patent Application No. 2016132716, filed on Aug. 8, 2016, the entire contents of which are incorporated herein by reference.

FIELD OF THE INVENTION

The present invention relates to the field of molecular biology, biochemistry and biotechnology, namely, to a compound of formula I, that is a derivative of usnic acid, and its spatial isomers:

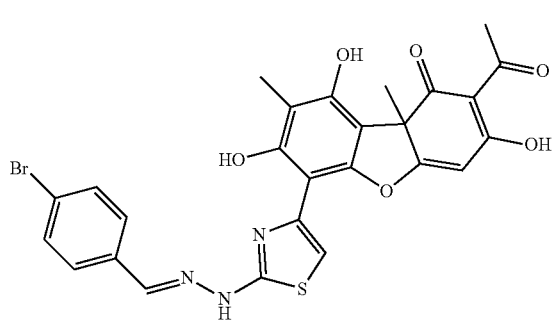

I which have a useful biological activity, namely, the ability to inhibit the action of human tyrosyl-DNA phosphodiesterase 1 enzyme (Tdp1).

BACKGROUND OF THE INVENTION

Figure 1:
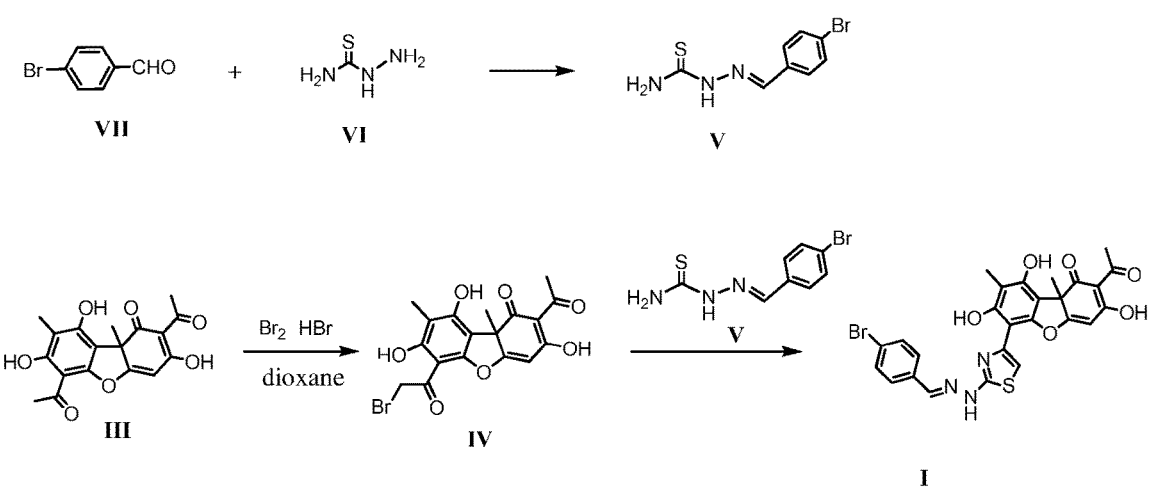
FIG. 1 is a depiction of a chemical scheme for the synthesis of a derivative of usnic acid of formula I.

Currently, there is considerable interest in the development of inhibitors of Tdp1 enzyme, which is considered a promising target enzyme for the development of drugs for treating oncological and neurodegenerative diseases [1].

Tdp1 is a phosphodiesterase, a class of enzymes which breaks phosphodiester bonds [2]. Tdp1 plays an important role in repairing the DNA damage induced by topoisomerase 1 (Top1) inhibitor camptothecin and other antitumor drugs. The normal enzymatic cycle of Top1 includes a reversible transesterification reaction. Tyrosine-723 residue of the enzyme's active center forms a transient covalent complex with 3'-phosphate of the DNA backbone, creating a single strand break, which allows the «broken» strand to rotate around the intact one, relaxing the local tension in the DNA helix. Then the integrity of the DNA is restored by a reverse reaction (ligation). In normal conditions the speed of ligation reaction is far greater than the breaking reaction, but in some cases the transient complexes remain stable. In particular, Top1 inhibitors, such as camptothecin and its clinically used derivatives, considerably slow down the ligation reaction [3]. The inability to restore the DNA structure results in single-strand breaks, which can subsequently turn into more toxic double-strand breaks. In addition to inhibitors, certain damage of DNA near the Top1 attachment site can also block the ligation reaction.

Tdp1 breaks the 3'-diester bond between the tyrosine residue and the 3'-end of the DNA, while also removing other types of damage from the 3'-end of the DNA [4,5]. At the same time, a phosphate remains at the 3'-end of the DNA, while a hydroxyl residue remains at the 5'-end. Such structure is a substrate for polynucleotide kinase 3'-phosphatase (PNKR) enzyme, which restores the 3'-OH, 5'-phosphate configuration, traditional for base excision repair (BER) [6]. As a result, Tdp1 reduces the efficacy of Top1 inhibitors, which are otherwise rather effective as anticancer drugs (see reviews [7, 8]). It is theorized that Tdp1 is responsible for the drug resistance of several types of cancer [3, 9]. This theory is confirmed by several studies: mice with Tdp1 knockout and human cell lines with SCAN1 mutations are hypersensitive to camptothecin [10-13]. On the other hand, camptothecin and etoposide induce less DNA damage in cells with increased level of Tdp1 expression [14, 15]. Thus, combining drugs acting on Top1 and Tdp1 can considerably increase the efficacy of chemotherapy.

It is also known that inhibiting Tdp1 activity makes tumor cells hypersensitive to anticancer drugs temozolomide (purine methylation) [16], methyl methanesulfonate (generation of apurinic/apyrimidinic site sites), bleomycin (single-strand/double-strand breaks with 3'-phosphoglycolates), hydrogen peroxide and ionizing radiation (strand breaks and other types of damage) [17]. This demonstrates that Tdp1 participates in different pathways of DNA repair.

Thus, Tdp1 inhibitors may be therapeutically useful for selectively enhancing the activity of antitumor drugs.

There are relatively few Tdp1 inhibitors described in the literature [18-28]. A major drawback of the known compounds is their relatively low inhibition potency towards Tdp1 ($IC_{50}$ ranges from 0.2 to 100 μM).

The compound, most similar to the present invention (a prototype), is furamidine, a heterocyclic diamidine [20] of formula II:

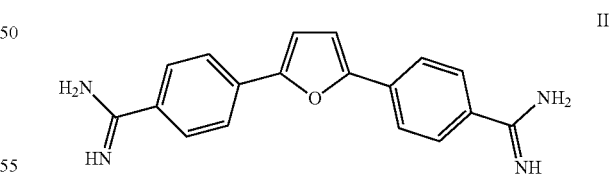

II

A drawback of this compound is its low inhibition potency towards Tdp1 ($IC_{50}$ for single-strand DNA is about 100 μM).

DETAILED DESCRIPTION OF THE PRESENT INVENTION

The goal of the present invention is the development of a more effective Tdp1 inhibitor based on usnic acid.

Usnic acid (III) is a metabolite of unique and available lichen species.

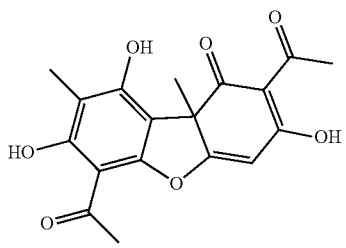

Usnic acid

Antibacterial, fungicidal and antioxidant properties of usnic acid are well known, but there is also recent data about the activity of usnic acid and its derivatives towards the repair enzyme PARP1 [28].

The goal is achieved by the disclosed compound, a hydrazine-thiazole derivative of usnic acid of formula (I) with high inhibition potency towards Tdp1 ($IC_{50}$ 0.026±0.011 µM).

Technical result: increase in inhibitory action towards Tdp1 and increase in the number of inhibitors of this enzyme.

The compound of the present invention can be synthesized in accordance with the schemes indicated at FIG. 1.

The starting compound is usnic acid with structural formula (III), produced by extracting it from a mixture of lichen using the method in [29]. A bromine-substituted derivative of usnic acid (compound IV) and thiosemicarbazone V are produced to be used to produce the target compound. Bromination of usnic acid (III) by bromine in the presence of hydrobromic acid is performed using the method in [30], resulting in compound IV. Thiosemicarbazone V is produced by interacting thiosemicarbazide (compound VI) with 4-bromobenzaldehyde VII using the method in [31], spectrum data is compared to that present in the literature. Finally, compound I with target activity is produced by interacting compound IV with thiosemicarbazone V with its subsequent purification by column chromatography.

More specifically, the production method of compound I is the following.

At the first stage, usnic acid is produced by extracting air dried raw material (lichen mixture) with chloroform while boiling with subsequent extraction of pure usnic acid in the form of yellow crystals by recrystallization from the chloroform:ethanol mixture (1:10). The obtained usnic acid (III) is brominated using a complex of bromine and dioxane (2 mmol of bromine dissolved in 14 ml of dioxane) in the presence of several drops of hydrobromic acid during 7 days in darkness at room temperature. After concentrating the reaction mixture at a rotary evaporator and performing column chromatography, a bromine-substituted derivative of usnic acid (IV) is produced. Then 4-bromobenzaldehyde thiosemicarbazone V is synthesized by slowly, dropwise, adding an alcohol solution of 4-bromobenzaldehyde VII to an aqueous solution of thiosemicarbazyde (compound VI). The resulting precipitate is washed by water, filtered and dried on air, it is subsequently used without purification. Synthesis of compound I is performed by boiling equimolar quantity of compound IV and 4-bromobenzaldehyde thiosemicarbazone V in ethanol during 1 hour, producing, after purification by column chromatography, compound I with yield 66%.

The structure and purity of the obtained compound I is confirmed by NMR spectroscopy and mass spectrometry.

The compound of formula (I) is a hydrazine-thiazole derivative of usnic acid.

After detailed pharmacological research, the compound (I) may be used for subsequent development of new, highly effective, low-toxic anticancer drugs.

Listed below are specific examples of the present invention.

Example 1. Synthesis of Compound I

A bromine-substituted derivative of usnic acid (IV) is synthesized using the method in [30]. For this a complex of bromodioxane (2 mmol (0.10 ml) of bromine was dissolved in 14 ml of dioxane) and several drops of HBr were added to 1 mmol of usnic acid III (344 mg) and left for 7 days at room temperature. After concentrating the reaction mixture at a rotary evaporator, the resulting precipitate was chromatographed on silica gel (60-200 µm), eluent—$CH_2Cl_2$. Yield 283 mg (67%). Then thiosemicarbazone V is synthesized using the method in [32]. For this 2 mmol (370 mg) of parabromobenzaldehyde were dissolved in 5 ml of ethanol and slowly, dropwise, added 2 mmol of aqueous solution of thiosemicarbazyde (VI) while stirring at room temperature. The resulting white precipitate was filtered, washed with distilled water and dried on air. Yield 392 mg (76%).

The 1 mmol (423 mg) of bromine-substituted derivative of usnic acid (IV) was added into 1 mmol (258 mg) of 4-bromobenzaldehyde thiosemicarbazone (V) and boiled in 10 ml of ethanol during 1 hour. The solvent was evaporated and the reaction mixture was chromatographed on $SiO_2$, eluent—methylene chloride.

The result was a hydrazine-thiazole derivative of usnic acid, 2-acetyl-6-(2-(2-(4-bromobenzylidene)hydrazinyl)thiazole-4-yl)-3,7,9-trihydroxy-8,9b-dimethyldibenzo[b,d]furan-1(9bh)-one (I) as a yellow-brown amorphous powder with yield 66% (437 mg).

$^1$H NMR ($CDCl_3$): 18.80 (1H, s, OH-3), 12.56 (1H, s, OH-7), 10.28 (1H, s, OH-9), 9.02 (1H, bs, NH), 7.37 (1H, d, J 8.3, 2H), 7.30 (1H, s, H-17), 7.29 (2H, d, J 8.3, H-19, H-23), 7.08 (1H, s, H-14), 5.82 (1H, s, H-4), 2.65 (3H, s, H-12), 2.18 (3H, s, H-10), 1.63 (3H, s, H-15). $^{13}$C NMR ($CDCl_3$): 201.3 (C-11), 198.0 (C-1), 191.5 (C-3), 180.2 (C-4a), 166.1 (C-16), 156.2 (C-5a), 151.5 (C-7), 151.2 (C-9), 143.5 (C-13), 141.0 (C-17), 132.3 (C-18), 131.7 (2C, C-20, C-22), 127.9 (2C, C-19, C-23), 123.8 (C-21), 108.8 (C-8), 105.3 (C-2), 104.8 (C-14), 103.6 (C-9a), 97.6 (C-6), 97.2 (C-4), 59.2 (C-9b), 32.1 (C-15), 27.8 (C-12), 8.4 (C-10). HRMS, found: m/z 583.0219 $[M]^+$ $C_{26}H_{20}N_3O_6{}^{81}Br_1S_1$. Calculated: 581.0251.

Example 2. Assessment of the Disclosed Compound's Action on Tdp1 Activity

Recombinant human tyrosyl-DNA-phosphodiesterase 1 (EC number 3.1.4.) was expressed in an *Escherichia coli* system (plasmid pET 16B-Tdp1 provided by Dr. K. W. Caldecott, Sussex University, UK) and isolated as described in [2, 32]. The reaction of removing Black Hole Quencher 1 (BHQ1) from 3'-end of an oligonucleotide, catalyzed by Tdp1, is used as the test system for determining the inhibitory properties of the test compounds. At the 5'-end of an oligonucleotide there is (5,6)-FAM, a fluorophore whose fluorescence intensity increases after removing the quencher. POLARstar OPTIMA fluorimeter (BMG LABTECH) was used to measure fluorescence.

The reaction mixtures (volume 200 µl) contained the buffer (50 mM Tris-HCl, pH 8.0; 50 mM NaCl; 7 mM mercaptoethanol), 50 nM oligonucleotide and different concentrations of the inhibitor. The reaction was initiated by adding Tdp1 to a final concentration of 1.3 nM. The measurements were performed in linear range of dependence of reaction rate to time (up to 8 minutes) each 55 seconds. The action of the disclosed compounds was assessed by $IC_{50}$ value (concentration of an inhibitor that reduces an enzyme's activity by half). $IC_{50}$ value was calculated using MARS Data Analisys 2.0 software (BMG LABTECH).

Figure 2:
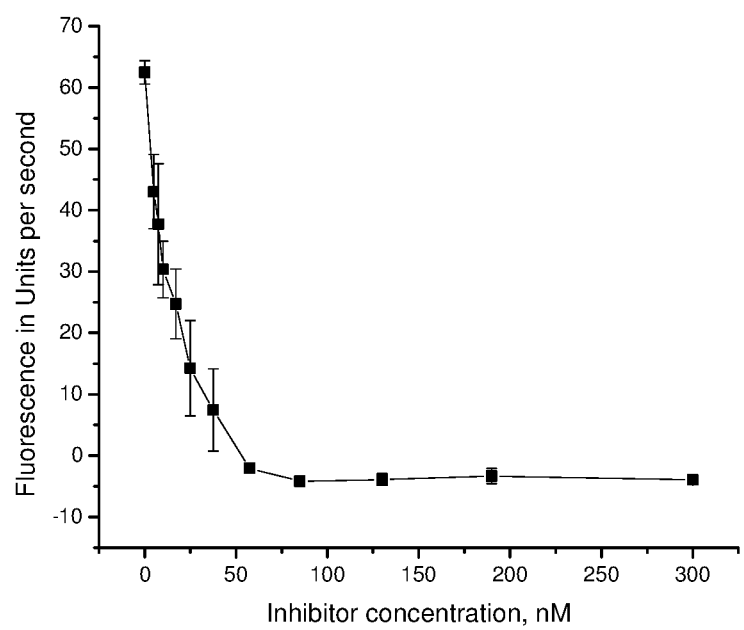
FIG. 2 is a depiction of the dependence of the chemical reaction rate, catalyzed by Tdp1, on the concentration of the inhibitor, a derivative of usnic acid of formula I.

A typical curve of relation of inhibitor concentration to the rate of reaction, catalyzed by Tdp1, is presented at FIG. 2. $IC_{50}$ of the disclosed compound is 0.026±0.011 μM, which is almost 4000 lower than that of the prototype compound.

Example 3

Assessment of acute toxicity of the disclosed compound was performed using outbred male CD-1 mice with SPF status. The test compound was administered in 62.5 mg/kg, 125 mg/kg, 250 mg/kg, 500 mg/kg, 1000 mg/kg, 2000 mg/kg and 5000 mg/kg doses (5 animals per group) in 0.5 ml volume once orally as a suspension in 0.5% aqueous solution of carboxymethyl cellulose. In all groups there was no animal mortality. Thus, the study demonstrates that maximal tolerated dose in no less than 5000 mg/kg, while $LD_{50}$ is over 5000 mg/kg (per os, male mice).

Thus, a low-toxic compound is disclosed, an usnic acid derivative of formula (I) which has a useful biological activity, namely, the ability to inhibit the action of human tyrosyl-DNA phosphodiesterase 1 enzyme (Tdp1).

The disclosed compound has a specific inhibitory action towards human tyrosyl-DNA phosphodiesterase 1 enzyme (Tdp1) and, being an effective inhibitor, increases the number of inhibitors of this enzyme and may be used to develop clinically useful drugs.

REFERENCES

1. Cortes Ledesma F., et al., Nature, 2009, 461, 674-678.
2. Interthal H., et al., Proc. Natl. Acad. Sci. U.S.A. 2001, 98, 12009-12014.
3. Dexheimer T S, et al., Anticancer Agents Med Chem. 2008, 8, 381-389.
4. Ben Hassine S, et al., The EMBO Journal, 2009, 28, 632-640.
5. Povirk L F. ISRN Mol. Biol., 2012, 1-16.
6. Vance J R, Wilson T E. J. Biol. Chem., 2001, 276, 15073-15081.
7. Pommier Y. Nat. Rev. Cancer, 2006, 6, 789-802.
8. Pommier Y., et al. Chem Biol., 2010, 17, 421-433.
9. Beretta G L, et al., Curr. Med. Chem. 2010, 17, 1500-1508.
10. El-Khamisy S F, et al., DNA Repair (Amst)., 2009, 8 760-766.
11. Das B B, et al., The EMBO Journal, 2009, 28, 3667-3680.
12. Katyal S., et al., EMBO J., 2007, 26, 4720-4731.
13. Hirano R., et al., EMBO J., 2007, 26, 4732-4743.
14. Barthelmes H U, et al., J Biol Chem. 2004, 279, 55618-25565.
15. Nivens M C, et al., Cancer Chemother Pharmacol., 2004, 53, 107-115.
16. Alagoz M., et al., Nucleic Acids Res., 2014, 42, 3089-3103.
17. Murai J., et al., J Biol Chem. 2012, 287, 12848-12857.
18. Dexheimer, T. S., et al., Anticancer Agents Med. Chem. 2008, 8, 381-389
19. Cortes Ledesma, F., et al., Nature 2009, 461, 674-678.
20. Antony, S., et al., J. Med. Chem. 2012, 55, 4457-4478.
21. Conda-Sheridan, M., et al., J. Med. Chem. 2013, 56, 182-200.
22. Sirivolu, V. R., et al., J. Med. Chem. 2012, 55, 8671-8684.
23. Huang, S. N., et al., Expert Opin Ther Pat. 2011, 21, 1285-1292.
24. Davies, D. R., et al., J. Mol. Biol. 2003, 324, 917-932.
25. Marchand, C., et al., Mol. Cancer Ther. 2009, 8, 240-248
26. Zakharenko, A. L., et al., Rus. J. Bioorg. Chem. 2015, 41, 657-662.
27. Zakharenko, A. L., et al., Bioorg. Med. Chem. 2015, 23, 2044-2052
28. Zakharenko A., et al., Med. Chem., 2012, 8, 883-893.
29. Pat. RF 2317076; Byul. Isobret. [Invention Bull.], 2008, No. 5.
30. Luzina O. A., et al., Chemistry of Natural Compounds. 2012, 48 (3), 385-391.
31. Aslam, M. A. S., et al., European Journal of Medicinal Chemistry, 2011, 46, 5473-5479.
32. Lebedeva N. A., et al., FEBS Lett., 2011, 585, 683-686.

We claim:
1. 2-acetyl-6-(2-(2-(4-bromobenzylidene)hydrazinyl)thiazole-4-yl)-3,7,9-trihydroxy-8,9b-dimethyldibenzo[b,d]furan-1(9bh)-one of formula I:

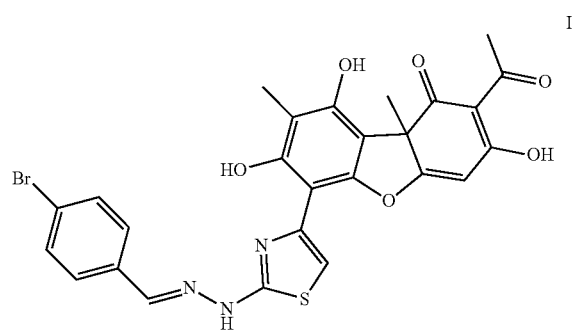 [SMILES: CC(=O)C1=C(O)C=C2Oc3c(-c4csc(N/N=C/c5ccc(Br)cc5)n4)c(O)c(C)c(O)c3C2(C)C1=O]

which has inhibitory action human tyrosyl-DNA phosphodiesterase 1 enzyme (Tdp1).

* * * * *